United States Patent [19]
Heald et al.

[11] Patent Number: 5,488,537
[45] Date of Patent: Jan. 30, 1996

[54] SAFETY INTERCONNECT LATCH FOR PORTABLE MEDICAL ELECTRONIC PATIENT MONITORING PRODUCT

[75] Inventors: Martin S. Heald, Beverly; Per O. Hoel, Magnolia, both of Mass.

[73] Assignee: Siemens Medical Systems, Inc., Iselin, N.J.

[21] Appl. No.: 218,394

[22] Filed: Mar. 28, 1994

[51] Int. Cl.⁶ ............................ H05K 7/10; H05K 7/11
[52] U.S. Cl. .................... 361/684; 439/374; 439/377; 439/929; 292/80; 292/87; 292/219; 361/683
[58] Field of Search ................... 439/374, 377, 439/929; 292/80, 219; 361/683, 684, 686, 732, 740, 747, 859180117251726

[56] References Cited

U.S. PATENT DOCUMENTS 3,017,469  1/1962  Giller ............................ 320/2
4,096,856  6/1978  Smith et al. .................. 128/4.19 D
4,113,217  9/1978  O'Connell ..................... 248/221.3
4,578,628  3/1986  Siwiak ............................ 320/2
5,103,997  4/1992  Shillington et al. ............ 220/481
5,248,264  9/1993  Long et al. ..................... 439/347

FOREIGN PATENT DOCUMENTS 2250054  5/1992  United Kingdom .

Primary Examiner—Leo P. Picard
Assistant Examiner—Phuong T. Vu
Attorney, Agent, or Firm—Lawrence C. Edelman

[57] ABSTRACT

A portable carrier module having a safety interconnect latch mechanism for securing the portable carrier module to a portable product. The portable carrier has a rail on one of its outer walls for engaging with a track on the portable product and for aligning the portable product to the portable carrier.

18 Claims, 4 Drawing Sheets

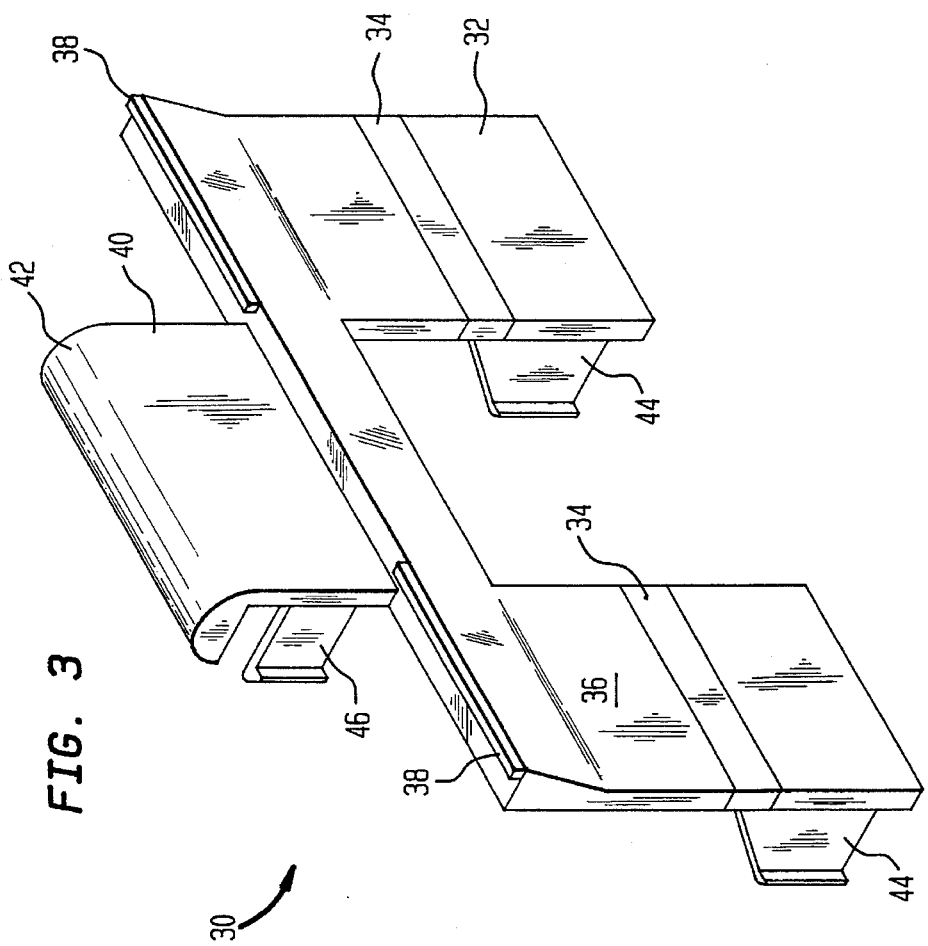
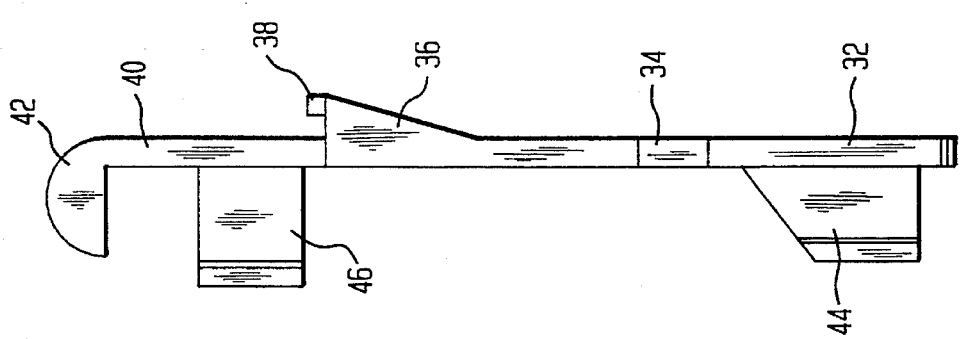

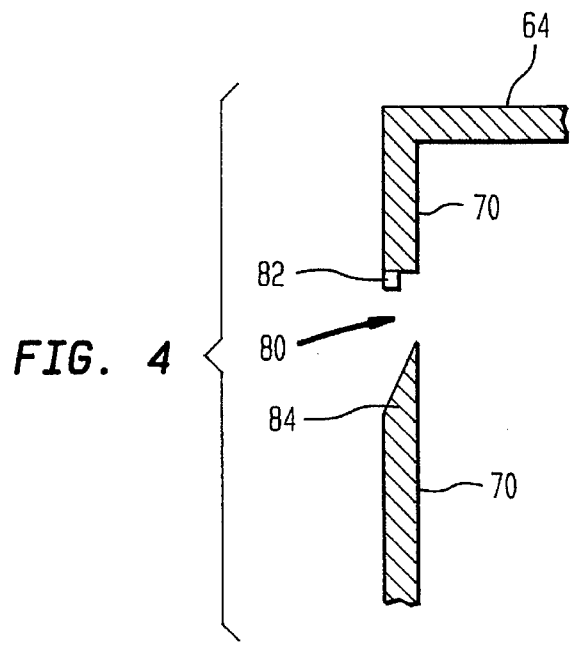
FIG. 4
FIG. 5
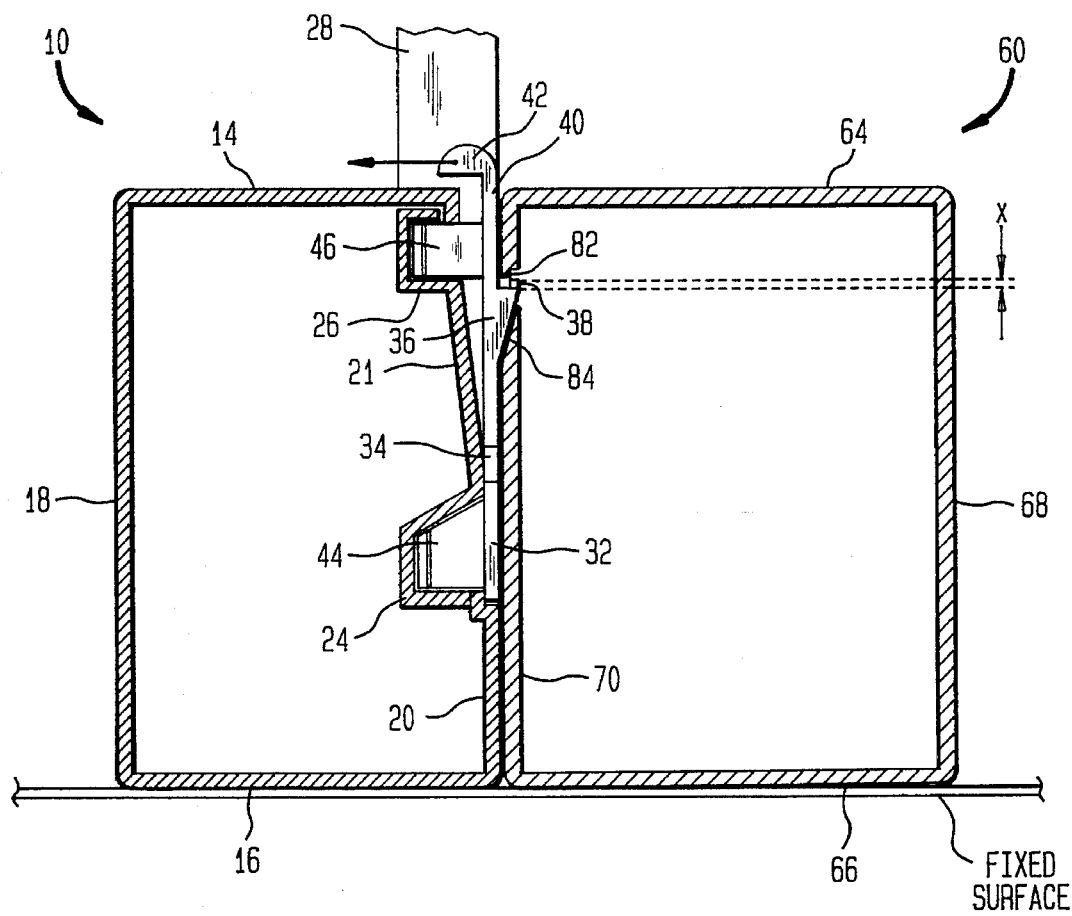

SAFETY INTERCONNECT LATCH FOR PORTABLE MEDICAL ELECTRONIC PATIENT MONITORING PRODUCT

BACKGROUND OF THE INVENTION

1. Field of the Invention

The present invention relates generally to the field of mechanical interconnect latch mechanisms and, more particularly, to a safety interconnect latch to secure a portable carrier module to a portable medical electronics module.

2. Background

Portable medical electronics and particularly for patient monitoring and care are becoming more and more mobile. It is often necessary in hospitals, health care facilities and at other locations to move portable medical electronics utilized in patient care from among many locations. One of the considerations in the design or selection of a portable medical electronic device is the speed and facility or ease in connecting and securing the portable electronic device to its carrier, typically a power source, as well as disconnecting one from the other in a safe and reliable fashion. As the patient is moved, or is changed from one level of care to another, a change or increase in monitoring results in the connection and disconnection of patient sensors as well as the associated supporting portable medical monitoring electronics. Whether during emergency or non-emergency conditions, the speed at which the supporting services are performed is affected by the ease of making the connection between the portable electronics module and its carrier, and the reliability and safety of the interconnection.

A need exists for a safety interconnect latch for accurately connecting and safely securing two portable components together.

Existing latch mechanisms require the performance of an affirmative act to secure the components together which increases the probability of failure to secure the components together, as well as rendering the coupling susceptible of inadvertent disengagement.

The need for improved safety interconnect latch is increased for the medical industry in which many portable products for patient monitoring are marketed as modular where a base unit and specialized modules are marketed and sold separately enabling the medical provider to configure the base unit and specialized units for particular applications. Some modular equipment requires the end user to mechanically connect the modules together typically with fasteners which requires a tool. Other modules are designed to connect together and require the user to take affirmative action to move a lever or switch in order to lock the units together. Although it is important that the user be able to connect the units together as quickly as possible, the user does not always have the time or the know-how to connect the units together, or to remember and execute a pre-established procedure required to fasten the modular units together.

It would an advantage over prior art design to obviate the need for any tool to connect the units together.

It would be a further advantage if the modular units slid together and the latch mechanism thereby became engaged.

It would be yet a further advantage if the units were latched together without the need for any affirmative action other than lifting the portable carrier unit.

SUMMARY OF THE INVENTION

A portable carrier for receiving a portable product adapted to having a recess forming a notch extending from an edge of the recess, the portable product further having a track on one of the plurality of external surfaces, the portable carrier comprising: a housing having a plurality of outer walls; a rail on one of the plurality of outer walls for engaging the track on the portable product and for aligning the portable product to the portable carrier; a latch assembly for insertion into the recess in the portable product, the latch assembly comprising: a shoulder portion adapted to fit into the recess of the portable product; a locking lip portion extending from the shoulder for engaging the notch of the portable product; a flexible member portion connected at one end to the shoulder and secured at another end to one of the plurality of outer walls and that allows the locking lip to move from a first position external to the recess to an intermediate position within the recess;

wherein when the rail on one of the plurality of outer walls engages the track on the portable product so as to align the portable product to the portable carrier, and the locking lip is in the intermediate position, and the portable carrier is elevated relative to the portable product, the latch assembly is caused to move to a locked position within the recess where the locking lip and notch are lockingly engaged whereby the portable carrier is locked to the portable product.

BRIEF DESCRIPTION OF THE DRAWINGS

FIG. 2 is a side view of the latch mechanism of the portable carrier module shown in FIG. 1 taken along line 2—2;

FIG. 3 is a perspective view of the latch mechanism shown in FIGS. 1 and 2;

FIG. 4 is a side view of a portion of the portable electronic patient monitoring module shown in FIG. 1 taken along line 4—4 showing a recess which receives the latch mechanism of the portable carrier module;

FIG. 5 is a cross-sectional view of the portable carrier module connected to the portable monitoring module and showing the latch mechanism engaged in an unlocked position within the recess of the portable monitoring module;

DETAILED DESCRIPTION OF THE INVENTION

Figure 1:
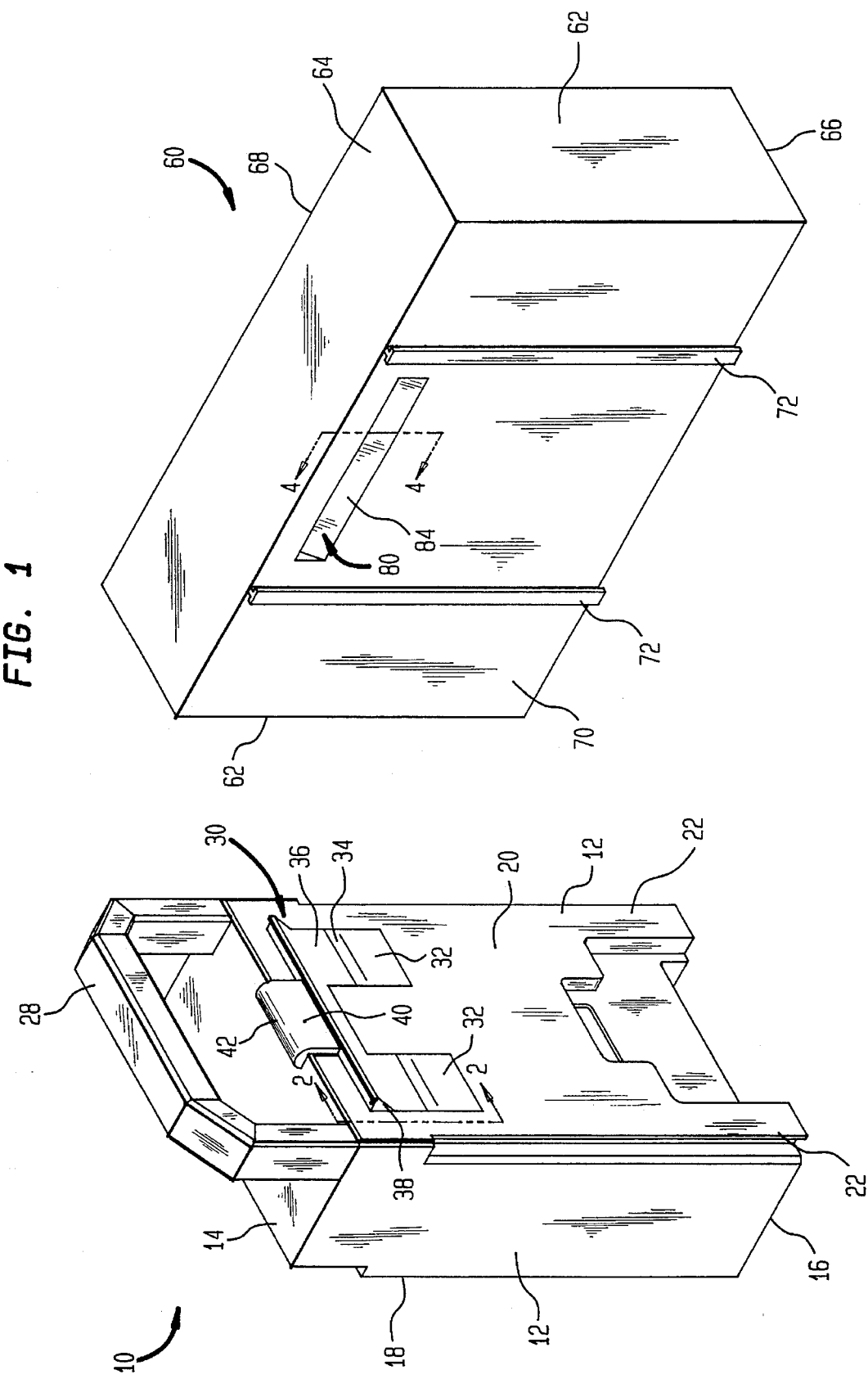
FIG. 1 is a perspective view of the portable carrier module and portable electronic patient monitoring module in accordance with the present invention.

Referring to FIG. 1, there is shown in perspective view a portable carrier module 10 and portable electronic patient monitoring module or portable product 60. Portable carrier module 10 includes a housing of sidewalls 12, top 14, bottom 16, front wall 18, rear wall 20, and a handle 28. Secured to rear wall 20 of the portable carrier module is a latch assembly mechanism 30, portions of which fit into and engage recess 80 in rear wall 70 of portable electronics module 60 when the two units are joined together. Rails 22 on rear wall 20 of portable carrier module engage tracks 72 on rear wall 70 of portable electronics module 60 for aligning and joining the portable carrier module to the portable electronics module, and for aligning the latch mechanism to the recess in the portable electronics module. Portable electronics module 60 further includes sidewalls 62, top 64, bottom 66, and front wall 68.

Latch mechanism 30 which is shown in FIGS. 2 and 3 includes two legs 32, two pivot or flexible members 34 each connected to a leg and which functions to allow the latch mechanism when secured to the portable carrier module to bend and flex, a shoulder 36 connected to each of the pivot members and secured to which is a locking lip 38. Although the particular configuration of the latch mechanism shown in FIGS. 1–3 includes two pivot or flexible members 34 each of which is connected to a corresponding leg 32 for securing to a wall of the portable carrier module, the latch mechanism of the present invention can include one flexible member connected at one end to the shoulder and secured at another end directly to a wall of the portable carrier module (not shown). Latch mechanism 30 also includes a neck 40 connected to shoulder 36 and upon which is mounted cap 42. Latch mechanism 30 further includes clips 44 connected to legs 32 and which fit into and are rigidly secured within corresponding recesses or slots 24 in rear wall 20 of portable carrier module 10 (FIG. 4b). Latch assembly 30 is shown as a one piece member which in a preferred embodiment is made of a flexible, elastic, and resilient plastic material to allow the latch assembly to pivot and flex at pivot members 34. In an alternative embodiment, latch assembly 30 is made of the above described members but are separate parts, including a pivot member made of an elastic and flexible material, and which are connected and joined together as described above.

Rear wall 70 of portable electronic module 60 is adapted to have a sloping edge 84 to match the contour of shoulder 36 of latch assembly 30 and is further adapted to include a notch 82 (FIG. 4a) for engaging locking lip 38 of latch assembly 30 when portable carrier module and portable electronics module are joined together.

Referring to FIGS. 1, 4b, and 5, operationally, when portable carrier module is to be secured and locked with portable electronic module for transport to a different position or location, portable carrier module 10 is lifted and positioned so that latch assembly 30 faces recess 80, and is lowered so that rails 22 on rear wall 20 are slid into tracks 72 of portable carrier module 60. Rails 22 and tracks 72 can be adapted to provide an electrical connection for power to be transferred from the portable carrier module to the portable electronics module, or for monitoring data to be transferred from the portable electronics module to the portable carrier module.

Figure 6:
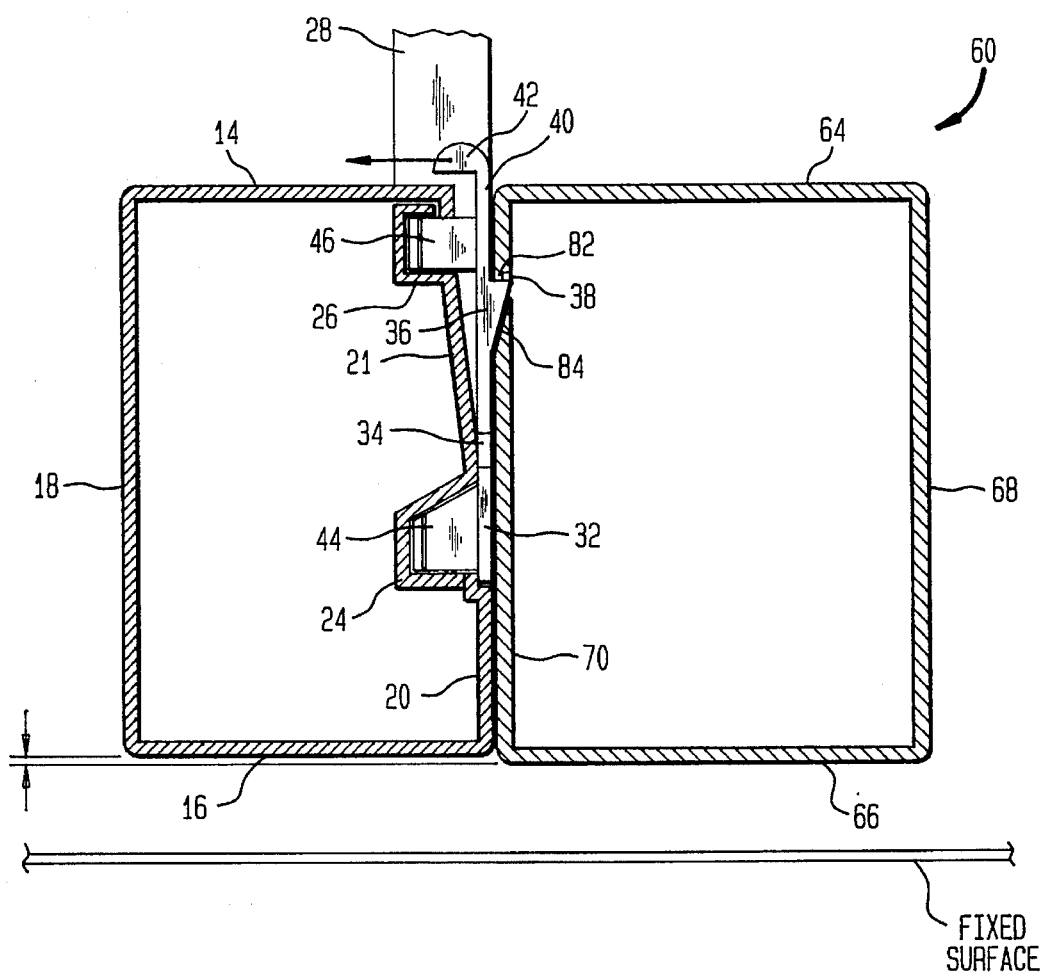
FIG. 6 is a cross-sectional the same view of the portable carrier module and portable monitoring module locked together after being lifted and showing the latch mechanism locked in engagement within the recess of the portable monitoring module.

As the portable carrier module is lowered onto and is slid along the tracks of the portable electronics module 60, shoulder 36 of latch assembly 30 comes into contact with rear walls 70 causing the shoulder 36 to be deflected perpendicular relative to the downward motion of the carrier module and out of the way. As the portable carrier module continues to be lowered into sliding engagement with the portable electronics module, shoulder 36 of the latch assembly passes notch 82 and springs into recess 80 of portable electronics module and into contact with sloping edge 84 of wall 70 as shown in FIG. 5. When the user then lifts the portable carrier module, locking lip 38 is simultaneously lifted a clearance distance relative to notch 82 (identified as x in FIGS. 5 and 6) before becoming fully engaged by notch 82, and thereby locking the portable carrier module to the portable electronics module (FIG. 6). Other than lifting the portable carrier module to lockingly engage it to the portable electronics module, the user need not take any action either in the form of securing the modules together by screws, bolts or the like, or by taking any other affirmative or active action such as pulling/pushing a component of either the portable carrier module or the portable electronic module. Thus, the modules passively or automatically become locked by the user merely lifting the carrier module after the portable carrier module is lowered into sliding engagement with portable electronic module as described above. In order to disengage the modules from one another, the user places the joined and locked modules on a surface causing the portable carrier module to travel the clearance distance x before coming to rest on the fixed surface. (FIG. 6). By placing the module on a flat surface, the height of the top of locking lip 38 is lower than the height of notch 82 thereby enabling the disengagement of the latch mechanism from the recess (FIG. 5). Since the modules are not locked together by the engagement of locking tip 38 with notch 82, the user pushes cap 42 toward the disengaging position as shown by the arrow in FIG. 5 causing shoulder 36 and locking lip 38 to withdraw from recess 80 whereupon the portable carrier module can be lifted along tracks 72 until the portable carrier module is disengaged and physically separated from the portable electronics module.

While the present invention has been particularly shown and described with reference to preferred embodiments thereof, it will be understood by those skilled in the art that various changes in form and details may be made therein without departing from the spirit and scope of the invention.

We claim:

1. A portable carrier for receiving a portable product having a recess forming a notch extending from an edge of the recess, the portable product further having a track on one of a plurality of external surfaces, the portable carrier comprising:

(a) a housing having a plurality of outer walls;
   (b) a rail on one of the plurality of outer walls for engaging the track on the portable product and for aligning the portable product to the portable carrier;
   (c) a latch assembly for insertion into the recess in the portable product, comprising:
      (1) a shoulder portion adapted to fit into the recess of the portable product;
      (2) a locking lip portion extending from the shoulder for engaging the notch of the portable product;
      (3) a flexible member portion connected at one end to the shoulder and secured at another end to one of the plurality of outer walls and that allows the locking lip to move from a first position external to the recess to an intermediate position within the recess;

wherein when (A) the rail on one of the plurality of outer walls engages the track on the portable product so as to align the portable product to the portable carrier and (B) the locking lip is in the intermediate position within the recess and (C) the portable carrier is elevated relative to the portable product, the locking lip is caused to move to a locked position within the recess where the locking lip and notch are lockingly engaged to lock the portable carrier to the portable product.

2. The portable carrier as in claim 1 wherein the latch assembly is a one piece member made of a flexible plastic.

3. The portable carrier as in claim 2 wherein the one of the plurality of outer walls to which the flexible member is secured is the one of the plurality of outer walls upon which the rail is positioned.

4. The portable carrier as in claim 3 wherein the latch mechanism further includes means for releasing the latch assembly from within the recess.

5. The portable carrier as in claim 4 wherein the means for releasing is a neck member connected to the shoulder for moving the locking lip from said intermediate position within the recess of the portable product to said first position external to the recess of the portable product.

6. The portable carrier as in claim 5 wherein said portable carrier contains an electric power source.

7. The portable carrier as in claim 6 further including an electrical connector for the transfer of power from the electrical power source to the portable product.

8. The portable carrier as in claim 7 wherein the electrical connector is the rail.

9. The portable carrier as in claim 1 wherein the portable carrier receives and stores monitoring data transferred from the portable product.

10. The portable carrier as in claim 1 wherein the flexible member portion is at least two flexible member portions and further includes two legs each of which is connected at one end to a corresponding one of the at least two flexible member portions and secured at another end to one of the plurality of outer walls.

11. The portable carrier as in claim 10 wherein the latch assembly is a one piece member made of a flexible plastic.

12. The portable carrier as in claim 11 wherein the one of the plurality of outer walls to which the legs are secured is the one of the plurality of outer walls upon which the rail is positioned.

13. The portable carrier as in claim 12 wherein the latch mechanism further includes means for releasing the latch assembly from within the recess.

14. The portable carrier as in claim 13 wherein the means for releasing is a neck member connected to the shoulder for moving the locking lip from said intermediate position within the recess of the portable product to said first position external to the recess of the portable product.

15. The portable carrier as in claim 14 wherein said carrier product contains an electric power source.

16. The portable carrier as in claim 15 further including an electrical connector for the transfer of power from the electrical power source to the portable product.

17. The portable carrier as in claim 16 wherein the electrical connector is the rail.

18. The portable carrier as in claim 10 wherein the portable carrier receives and stores monitoring data transferred from the portable product.

* * * * *